United States Patent [19]

Laurila et al.

[11] Patent Number: 5,888,249
[45] Date of Patent: Mar. 30, 1999

[54] FIBROUS MATERIAL AND METHOD FOR ITS MANUFACTURING

[75] Inventors: Maija Laurila, Espoo; Pirjo Vapaaoksa, Vantaa, both of Finland

[73] Assignee: Carefibres Oy, Espoo, Finland

[21] Appl. No.: 894,592

[22] PCT Filed: Feb. 23, 1996

[86] PCT No.: PCT/FI96/00109

§ 371 Date: Sep. 17, 1997

§ 102(e) Date: Sep. 17, 1997

[87] PCT Pub. No.: WO96/26313

PCT Pub. Date: Aug. 29, 1996

[30] Foreign Application Priority Data

Feb. 23, 1995 [FI] Finland .................................. 950829

[51] Int. Cl.$^6$ .................................................. D06M 13/432
[52] U.S. Cl. .............................. 8/111; 8/931; 252/186.26; 252/186.42; 424/402; 424/404; 424/70.1; 424/70.6; 132/208; 132/221; 132/222

[58] Field of Search .................. 8/111, 931; 252/186.26, 252/186.42; 424/402, 404, 70.6, 70.1; 132/208, 221, 222

[56] References Cited

U.S. PATENT DOCUMENTS

| | | | |
|---|---|---|---|
| 5,259,848 | 11/1993 | Terry et al. .................................. | 8/111 |
| 5,372,801 | 12/1994 | Malmros et al. ......................... | 424/7.1 |
| 5,417,752 | 5/1995 | Parén et al. .............................. | 106/168 |

FOREIGN PATENT DOCUMENTS

| | | |
|---|---|---|
| 1064271 | 7/1963 | United Kingdom . |
| WO 95/24525 | 9/1995 | WIPO . |

*Primary Examiner*—Alan Diamond
*Attorney, Agent, or Firm*—Pollock, Vande Sande & Amernick

[57] ABSTRACT

A fibrous material including a fibrous material, urea peroxide absorbed on the fibrous material, and a bicarbonate anion containing substance absorbed on the fibrous material.

20 Claims, No Drawings

FIBROUS MATERIAL AND METHOD FOR ITS MANUFACTURING

This application is a 371 of PCT/FI96/00109 filed Feb. 23, 1996.

FIELD OF THE INVENTION

The invention relates to a fiber structure containing urea peroxide and a method for its manufacturing. The fiber structure of the invention is used especially in hair bleaching.

BACKGROUND OF THE INVENTION

It has long been known that the sunlight together with the air causes natural bleaching of hair. Bleaching is based on the oxidation of color pigments in hair, which is effected by oxygen in the air and causes the transformation of the color pigments into achromatic substances.

Bleaching of hair is thus based on the oxidation phenomenon. In artificial hair bleaching, which is relatively much faster than the natural method, strongly oxidizing substances are used. A conventionally used bleaching agent is hydrogen peroxide. The effect of hydrogen peroxide on hair is both physical and chemical. It causes scale like cells on the surface of a hair to be detached from each other, whereby it can penetrate the hair. In the hair, the hydrogen peroxide oxidizes the melamine functioning as a pigment.

Hair can also be bleached with so-called rinsing solutions containing hydrogen peroxide and ammonium hydroxide or with bleaching shampoos containing these agents. However, hydrogen peroxide is not preserved long as a solution, which means that fresh solutions should always be used. Penetrating the hair with hydrogen peroxide can be made more effective by using a moisturizer, for example quaternary ammonium compounds. It is also possible to use tablets which in addition to hydrogen peroxide contain urea compounds. The tablets are dissolved in water immediately before the use.

Bleaching materials of emulsion or cream form can be used when it is desired to color only a certain amount of hair. Cream bases of these products contain macromolecular alcohols, fatty alcohol sulphonates etc. Instead of hydrogen peroxide it is possible to use sodium, potassium or ammonium persulphate. Quaternary ammonium compounds as a part of the cream bases facilitate the treatment of hair.

All bleaching materials used in hair treatment should be non-toxic, they should not have any harmful side effects and neither should they damage the hair.

However, by using said methods of prior art the hair is excessively strained. When bleaching with conventional methods it can be difficult to locate the bleaching particularly when making bleached stripes. Furthermore, the bleaching usually takes a rather long time. In addition, the person who treats the hair is exposed to dusty bleaching materials. Also, the odors formed in the work environment are quite strong when using conventional methods.

In a number of applications it is known to use urea peroxide as the source of oxygen. It has the effect that it retards the growth of bacteria and fungi; it can be used to eliminate odor etc. Furthermore, it can be used for bleaching.

The anti-bacterial and disinfecting properties of urea peroxide are utilized in the invention in accordance with Finnish patent application 941126. It presents a fiber structure containing urea peroxide and a method for its manufacture. The fiber structure according to Finnish Patent Application 941126 comprises a polysilicic acid containing fiber, having the urea peroxide absorbed therein. The fiber structure comprises a supporting structure which is advantageously of cellulose, preferably regenerated viscose cellulose, and polysilicic acid containing aluminium silicate sites or mere polysilicic acid homogeneously distributed in the same phase with the viscose cellulose. To absorb urea peroxide in polysilicic acid containing fiber structure has, for example the advantages, compared to ordinary, for instance viscose fibers, that the material lasts longer in the fiber patches, and better resistance to washing. The embodiments of the fiber structure presented in Finnish patent application 941126 include, for instance, the use of the material in hospitals. Another possible field of application mentioned there is hair bleaching for instance when making stripes in hair. However, no examples describing embodiments of the latter field of application is presented here.

The structure of the polysilicic acid containing fiber, or the so-called VISIL-fiber, and its manufacturing employed in the above mentioned application is presented in patent publication GB-1064271. The manufacturing and structure of the VISIL-fiber are also described in patent publication FI-91778. However, the invention presented in this publication primarily deals with a VISIL-fiber modified by using a compound containing aluminium, that is the so-called "VISIL-AP"-fiber. The present invention utilizes these fiber materials containing polysilicic acid. However, the invention is not limited to these fiber materials, instead any absorbent fiber material can be used, such as cellulose based fiber material, for instance viscose fiber.

As it has been mentioned earlier, the conventional methods for hair bleaching have many disadvantages. In addition, it has been noted that hair bleaching by using the VISIL-fiber patches in accordance with Finnish patent application FI-941126, in which patches of only urea peroxide is impregnated as the active agent, is too slow and inefficient.

SUMMARY OF THE INVENTION

The purpose of the present invention is to provide a product to be used in hair bleaching, which can be used to implement the bleaching quickly and easily and in a manner that the hair is not damaged.

Further, the purpose of the invention is to provide a product to be used in hair bleaching, which product is pleasant to use as to work hygiene and health, and which product does not form waste harmful to the environment.

Furthermore, it is the purpose of the invention to provide a product for hair bleaching which is of reasonably inexpensive material.

Another purpose of the present invention is also to present a method for manufacturing the above mentioned product.

Yet another object of the invention is to present a method for hair bleaching and a particular object of the invention is to present a method for making bleached stripes in hair.

It has now been noticed that hair bleaching, and particularly making bleached stripes in hair, may be easily and quickly implemented, in a manner that the treated hair is not strained, by using the bleaching fibrous material containing urea peroxide in accordance with the present invention. By using the bleaching material according to the present invention, the amount of odors and dusts spreading in the work environment also decreases to a significant degree. In accordance with the present invention, the polysilicic acid fibrous material containing urea peroxide is characterized in that a fibrous material of this type further contains as active agents a substance containing a bicarbonate anion, advantageously ammonium bicarbonate. The present invention includes advantageous options for the fibrous material, special characteristic features in the manufacturing of this material, and use of the fibrous material of the present invention in bleaching hair.

DETAILED DESCRIPTION OF THE INVENTION

The product according to the invention used for bleaching hair thus comprises the fibrous material in which the compounds producing the bleaching are absorbed. The bleaching of a desired area in hair is implemented by wrapping around the hair to be treated patches cut of the fibrous material. The bleaching material absorbed in the patches is let to influence the hair at a mild temperature for a suitable time, which is about 30 minutes.

Thus, it has now been noticed that the bleaching can be efficiently and quickly implemented and well allocated to the area to be bleached, with hardly any straining to the hair where the bleaching agent used in the bleaching fiber material is urea peroxide, in which has been added a substance containing a bicarbonate anion, such as sodium bicarbonate ($NaHCO_3$) or ammonium bicarbonate ($NH_4CO_3$). Substances are impregnated in the absorbent fiber which is capable of releasing the active agents in suitable using conditions. Advantageously, these substances are impregnated in the polysilicic acid containing fiber, that is the VISIL-fiber, which is described above.

An effective bleaching is provided by using bicarbonate, because $HCO_3$ and urea peroxide react with each other, wherein percarbonic acid is formed as the intermediate product, which produces the desired bleaching. Percarbonic acid is a non-permanent intermediate product and it is further decomposed to carbon dioxide and water. The flow of the reaction can be illustrated with the following reaction scheme, in which ammonium bicarbonate is used as an example:

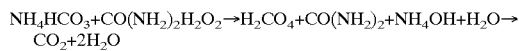
$$NH_4HCO_3 + CO(NH_2)_2H_2O_2 \rightarrow H_2CO_4 + CO(NH_2)_2 + NH_4OH + H_2O \rightarrow CO_2 + 2H_2O$$

The percarbonic acid, which is formed as the intermediate product, is less harmful to health and work hygiene than peroxide. The $NH_4$-ion which is present in the reaction in its turn facilitates the bleaching material to penetrate the hair.

In dry state, the urea peroxide is a white crystalline substance, which dissolves in water and alcohols. The substance decomposes at a temperature of about 75° to 78° C., when exposed to humidity even at about 40° C. Urea peroxide is inexpensive. Furthermore, it decomposes in composting when the temperature exceeds 40° C. and it becomes a part of nutritious soil.

The fibrous material used in hair bleaching is manufactured by absorbing the active agents in the fiber structure. The fiber structure is advantageously in a form of a planar textile structure, such as a non-woven cloth. The non-woven cloth can be formed of polysilicic acid containing fiber with a supporting structure possibly of cellulose, advantageously of regenerated viscose cellulose, in which the polysilicic acid is homogeneously distributed in the same phase; that is, it is so-called VISIL-fiber. Further, in the invention, it is possible to use other fibers in which polysilicic acid is bound, for instance polysilicic acid containing synthetic fibers, in which polyester forms the supporting structure. However, the relatively inexpensive costs of the polysilicic acid containing viscose fiber make it the most advantageous alternative. In addition, it is also possible to use other absorbent fibers which can be synthetic, natural fibers or of regenerated cellulose.

With regard to the purpose of use of the present invention it is most advantageous to manufacture the fibrous material patches of desired size, in which the active bleaching substances, that is the urea peroxide and bicarbonate, are then impregnated by immersing the patches into these solutions one after the, other or by spraying the solution to the patches. After each immersion or spraying phase the patches are dried, in order to prevent the substances from reacting with each other too early. The urea peroxide used for impregnation can be manufactured before the impregnation by mixing urea peroxide solution and hydrogen peroxide solution with each other or by dissolving urea peroxide crystals in the impregnation solution. Experiences indicate that a solution obtained by the latter method is of a more uniform and stable quality. Further, it is possible to bring the material into contact with the latter solution in wet state, after which drying is made quickly. Furthermore, it is possible to absorb the active agents at one time from the same solution, which has been kept in good conserving conditions (at a low temperature) or manufactured immediately before the absorption. It is also possible to absorb hydrogen peroxide to a fiber impregnated with urea, in conditions in which the urea peroxide can be formed in connection with the absorption.

It is self-evident to an expert in the field that the active agents can be impregnated according to the corresponding principles in a larger quantity of fibrous material, and patches of a suitable sizes can be cut a thereof. It is to be noted the changes taking place with time in the bleaching efficiency of the active agents of the material which is kept moist. This issue is further discussed below.

In the bleaching urea, peroxide containing fiber material of the present invention, urea peroxide is impregnated from a solution of about 10 to 30%, advantageously about 15 to 25 %, and ammonium bicarbonate from a solution of about 1 to 20 %/, advantageously about 2 to 15%. Correspondingly, it is noticed that using such concentrations, the remaining quantities of the dry weight of fiber in the VISIL-fiber is about 0.30 to 0.56 weight % urea peroxide, advantageously about 0.39 to 0.52 weight %, and about 0.041 to 0.46 weight % ammonium bicarbonate, advantageously about 0.080 to 0.39 weight %. Particularly good results in bleaching are obtained when the proportions in the solution impregnated in the fiber patches were about 20% urea peroxide and about 10% ammonium bicarbonate. The concentrations of the active agents in VISIL-fiber can be adjusted by modifying the concentrations of the urea peroxide solutions and the ammonium bicarbonate solutions, by modifying the relation of the fibrous material to the solution quantity and/or by adjusting the retention time of the fibrous material in the solution. The values mentioned above are suggestive for the values obtained when alkali metal bicarbonates are used.

Instead of ammonium bicarbonate other bicarbonates can be used, for instance sodium bicarbonate. Further, additives known in bleaching agent mixtures can be used in the fibers.

If particularly bleached stripes in hair are desired, the fiber patches are preferably for instance strips of the size 15×5 cm, which are easy to wrap on the treated area of hair. On the patches also aluminium foil or plastic foil can be wrapped in order to prevent the active agents and moisture from evaporating. The effect of the bleaching substances is improved for instance by using a heating lamp. A sufficient treating time is about 20 to 40 min. Finally, the bleached hair is washed and rinsed with excess water. The result by using the method in accordance with the invention is excellently bleached hair, the structure of which has remained intact and the condition of which corresponds untreated hair.

The stability of the effectiveness of the bleaching substances used in the bleaching fiber patches according to the present invention was studied. In the study, it was noticed that the solution formed of bleaching substances (urea peroxide and ammonium bicarbonate) preserved well at refrigerator temperatures even for several weeks. On the other hand, patches moisturized with this solution lost their bleaching efficiency by the next day. According to the performed tests, it is also possible to "pre-fabricate" bleaching patches in a manner such that the fiber patches are impregnated solely with urea peroxide and the patches are subsequently dried at a temperature under 40° C. and the dried patches are kept at room temperature. These pre-fabricated patches are not moisturized until immediately before use with ammonium bicarbonate. The efficiency of these patches was equal with the efficiency of the patches manufactured right before use.

In addition, it was generally noticed that the bleaching efficiency was improved by raising the pH-value, because the base opens hair scales and thus helps the active agent to operate better. The pH-value of the impregnation solution containing bicarbonate is adjusted with base to be over 8.5, advantageously between 8.8 and 9.2.

In the following examples the present invention is described more closely. However, the examples are not to be considered to limit the invention but only to clarify the objects of the present invention.

EXAMPLE 1

Reference Example

A material containing 60 g/m² VISIL non-woven cloth was manufactured by absorbing urea peroxide solution in the material. Urea peroxide was manufactured by dissolving urea in water of room temperature and by adding hydrogen peroxide. The non-woven cloth was cut in pieces of about 15×5 cm and urea peroxide solution, containing 20% urea peroxide, was impregnated in them. The moisturized fiber was used immediately and wrapped on a hair sample. The fiber and hair sample was wrapped in plastic foil or aluminium foil and the sample was kept at an incubator with a temperature of 40° C. for 20 to 40 min. After this treatment the hair was removed from the wrapping and it was rinsed in excess water. As a result, only slightly bleached hair samples were obtained.

EXAMPLE 2

A fibrous material in accordance with Example 1 was manufactured, with the difference that the solution contained 20% urea peroxide and 2% ammonium bicarbonate, and the hair was treated in a corresponding manner as in Example 1. As a result, it was obtained bleached hair that had better condition and looked better than the hair treated with conventional methods.

EXAMPLE 3

A fibrous material in accordance with Example 1 was manufactured by using a solution containing 20% urea peroxide and 10% ammonium bicarbonate, and the hair was treated in a corresponding manner as in Example 1. As a result, it was obtained hair that was very well bleached and had better condition and looked better than the hair treated with conventional methods.

EXAMPLE 4

A fibrous material in accordance with Example 1 was manufactured by using a solution containing 20% urea peroxide and 10% ammonium bicarbonate and living hair on the scalp was treated according to Example 1. The head of test subject was kept under a heating lamp about 30 min. The hair was washed after the treatment and excellent stripes were obtained as a result. The hairs in the stripes, that is the bleached hair, looked and felt equally good as the cut and bleached hair samples.

EXAMPLE 5

The composition of an impregnation solution containing known additives:

| Urea peroxide | 10% |
| --- | --- |
| NH$_4$HCO$_3$ | 9% |
| NH$_4$OH | 1.5% (pH adjustment) |
| "TURPINAL 4NL" | 1% |

"TURPINAL 4NL" is a solution manufactured by Henkel KGaA and used as a stabilizer of hydrogen peroxide, in which solution the active agent is tetrasodium etidronate at a concentration of 29 to 31% which forms a complex with the interfering metals.

EXAMPLE 6

When using sodium bicarbonate instead of ammonium bicarbonate it was obtained also a clear bleaching effect, which did not appear to be as strong as by using ammonium bicarbonate.

EXAMPLE 7

The stability of urea peroxide was tested by manufacturing fiber patches in three different methods:

1) It was manufactured fiber patches in which the tested liquid had been impregnated. The patches were kept at refrigerator temperature and they were used for bleaching in predefined intervals.
2) A method according to 1), except that the patches were kept at room temperature.
3) Fibre patches were manufactured by absorbing them with the tested liquid immediately before use. The tested liquid was also kept at refrigerator temperature and the manufactured patches were used for bleaching in a corresponding manner as with the ready-impregnated patches in 1).
4) It was manufactured fiber patches which were impregnated with urea peroxide from a 30% solution without ammonium bicarbonate and the patches were dried. The dry patches were kept at room temperature and only before the bleaching test they, were impregnated with ammonium bicarbonate from a 10% solution.

The patches which were kept moist lost their activity already by the next day, whereas the patches made of a solution kept in a bottle immediately before use, as well as patches which had been kept dry for three weeks, hardly lost any of their activity.

In other words, the ready-made patches containing both active agents should be used relatively fresh. On the other hand, the moisturizing solution preserves well, even for several weeks, at a sufficiently low temperature, as well as do properly dried, pre-fabricated urea peroxide fiber patches, which are activated immediately before use with ammonium bicarbonate solution.

According to the results in preservation obtained for different fibrous materials and substance combinations it is also possible to define a best-before day for the actual product.

Although the invention is described above primarily in respect of hair bleaching, it can also be used in objects, in which anti-bacterial and disinfective properties of fibers are required, and especially in such objects, in which rapid oxidation by percarbonic acid is desired.

We claim:

1. A hair care product, comprising:
   a fibrous material;
   urea peroxide absorbed on the fibrous material; and
   a bicarbonate anion containing substance absorbed on the fibrous material.

2. The hair care product according to claim 1, wherein the bicarbonate anion containing substance is ammonium bicarbonate.

3. The hair care product according to claim 1, wherein the fibrous material is a polysilicic acid containing material.

4. The hair care product according to claim 3, wherein the fibrous material includes a supporting structure of cellulose, wherein the polysilicic acid is homogeneously distributed in the cellulose.

5. The hair care product according to claim 4, wherein the cellulose is regenerated viscose cellulose.

6. The hair care product according to claim 1, wherein the fibrous material includes 0.04% to 0.5% by weight of the bicarbonate anion containing substance and 0.3% to 0.6% by weight urea peroxide, wherein the percent by weight is based upon the dry weight of the fibrous material.

7. A fibrous material, comprising:
   a fibrous material;
   urea peroxide absorbed on the fibrous material; and
   a bicarbonate anion containing substance absorbed on the fibrous material.

8. A method for manufacturing a fibrous material, the method comprising the step of:
   treating a fibrous material with a solution containing urea peroxide and a solution containing bicarbonate to absorb the urea peroxide and bicarbonate in the fibrous material.

9. The method according to claim 8, wherein the bicarbonate solution is an ammonium bicarbonate solution.

10. The method according to claim 8, wherein the solution containing urea peroxide and the solution containing bicarbonate are the same solution.

11. The method according to claim 8, wherein the fibrous material is immersed in the urea peroxide solution and bicarbonate solution immediately prior to use.

12. The method according to claim 8, wherein the fibrous material is sprayed with the urea peroxide solution and bicarbonate solution immediately prior to use.

13. The method according to claim 8, wherein the fibrous material is treated first with the urea peroxide solution, the method further comprising the steps of:
   drying the urea peroxide treated fibrous material;
   maintaining the urea peroxide treated fibrous material in a dried state; and
   treating the urea peroxide treated fibrous material with a bicarbonate solution immediately prior to use.

14. The method according to claim 8, wherein the solution containing urea peroxide includes from 10% to 30% by weight urea peroxide and the solution containing the bicarbonate includes from 1% to 20% by weight bicarbonate.

15. The method according to claim 8, wherein the solution containing urea peroxide includes from 15% to 25% by weight urea peroxide and the solution containing the bicarbonate includes from 2% to 15% by weight bicarbonate.

16. The method according to claim 8, further comprising the step of:
   cutting the fibrous material into patches prior to treating the fibrous material.

17. The method according to claim 16, wherein the patches are strips.

18. A method for bleaching hair, the method comprising the step of:
   contacting hair with a fibrous material containing urea peroxide and bicarbonate.

19. The method according to claim 18, further comprising the steps of:
   permitting the fibrous material to contact the hair for 20 to 40 minutes;
   separating the hair and the fibrous material; and
   rinsing the hair.

20. The method according to claim 18, wherein the hair is bleached in stripes.

* * * * *